United States Patent [19]
Russell

[11] Patent Number: 5,873,827
[45] Date of Patent: Feb. 23, 1999

[54] SURFACE MARKER FOR ULTRASOUND EXAMINATION AND A METHOD FOR USING THE MARKER

[76] Inventor: Donald G. Russell, 86 Windsor Rd., Kensington, Conn. 06037

[21] Appl. No.: 774,130

[22] Filed: Dec. 23, 1996

[51] Int. Cl.⁶ ........................................ A61B 8/00
[52] U.S. Cl. ............................................ 600/437
[58] Field of Search ............ 128/660.01, 662.02, 128/662.05; 600/437, 442, 458, 461

[56] References Cited

U.S. PATENT DOCUMENTS

| | | |
|---|---|---|
| 4,116,074 | 9/1978 | Jensen . |
| 4,183,353 | 1/1980 | Gallub . |
| 5,161,536 | 11/1992 | Vilkomerson et al. . |
| 5,184,622 | 2/1993 | Tomura . |
| 5,201,314 | 4/1993 | Bosley et al. ............ 128/662.02 |
| 5,226,419 | 7/1993 | Hanrahan et al. . |
| 5,349,958 | 9/1994 | Hanrahan et al. . |
| 5,383,466 | 1/1995 | Patrika . |
| 5,495,852 | 3/1996 | Stadler et al. . |

*Primary Examiner*—Francis Jaworski
*Attorney, Agent, or Firm*—McCormick, Paulding & Huber

[57] ABSTRACT

The invention provides a surface marker for use in ultrasonography. The marker comprises a material which attenuates a portion of the ultrasound energy applied to an ultrasound field including the marker and tissue underlying the marker. When placed on the surface of the skin above a particular tissue structure and then imaged, the marker projects a shadow of reduced sonic energy into the underlying tissue structure. The shadow provides direct visual evidence that the tissue beneath the marker has been imaged. The shadow projected by the marker may also be used to locate the image of an area of particular clinical interest within the tissue structure, such as a tumor or cyst.

14 Claims, 2 Drawing Sheets

SURFACE MARKER FOR ULTRASOUND EXAMINATION AND A METHOD FOR USING THE MARKER

FIELD OF THE INVENTION

The present invention relates to a surface marker for use in medical ultrasonography. The marker is applied to the surface of the skin and is imaged along with the underlying tissue during an ultrasound examination.

BACKGROUND OF THE INVENTION

High resolution ultrasonography utilizes appropriate low energy sound waves to assess the sound transmission and reflective qualities of human tissue. Ultrasound images are formed by means of echoes among tissues with different acoustic impedance. Acoustic impedance is the product of sound speed and bulk modulus. The bulk modulus expresses the elasticity of an object, and in the human body the value is increased by conditions such as fibrosis and calcification. The sound speed is usually high in elastic tissues and low in water. In the body, it is lowest in the fatty tissues. When ultrasound passes through tissue, it is absorbed as thermal energy and attenuated. When the attenuation rate increases, the posterior echoes are attenuated. However, in tissues with a high water content, such as cysts, the posterior echoes are accentuated.

The machines used for ultrasound examination include a hand-held transducer which houses a crystal that is vibrated electronically. The transducer is placed on the surface of the patient's skin, and the ultrasound produced by the vibrating crystal penetrates the underlying tissue. The returning echoes are displayed as a digital image that represents the intensity of the ultrasound echoed or reflected by the underlying tissue. The tissue is examined in a series of very thin vertical sections or slices, and the depth of any particular tissue element within a section is determined according to the time it takes an echo reflected from that element to return to the transducer.

Modern ultrasound machines have a feature that is referred to as "real time". This consists of a linear array of separate transducers which are activated sequentially and which transmit successive waves of sound. This feature permits the detection of motion of anatomic parts, such as the expansile pulsation of blood vessels. In obstetrical applications, this ability to detect motion permits recognition of early fetal heart activity and, later, movement of fetal extremities.

In performing an ultrasound examination, the technologist first applies a thick layer of an aqueous gel to the surface of the skin above the tissue area of interest. It is a well-known to those skilled in the art of ultrasonography that while water transmits sound very well, most ultrasound detail lying beneath an air layer or pocket will be obscured. The gel replaces the air at the skin's surface and allows a direct fluid connection between the transducer and the skin.

After the gel has been applied to the area of interest, the technologist moves the transducer through the gel while studying the images on a video monitor. The images are also stored on a permanent recording medium, such as film, a laser print or a photograph. It is important to recognize that, currently, ultrasound examinations are conducted without reference to any consistent, fixed, reproducible or definable landmarks. Only the technologist knows the position and orientation of the transducer when an image is recorded. There are of course standard views, and a serious attempt is made to do transverse and longitudinal scans in some order, but ultrasonagraphy is basically a free hand study.

The surface position of the ultrasound transducer is, by custom, recorded in hand written notes during or after the image is made. Accordingly, the surface position of the transducer is described in a general relationship to well-known or visible surface anatomy or to other descriptive clinical findings. (E.g., "above and lateral to navel" or "below and lateral to palpable mass"). In state of the art equipment, this general information may be inscribed electronically onto the image with accompanying brief references during or after the examination. Later, when the film from the examination is being interpreted, the interpreter must accept the technologist's handwritten and/or electronic notes regarding the position of the transducer as factual. However, in the event that the area being examined is of clinical interest, there is no clear visible evidence included in the image indicating that the transducer is positioned over this area.

It is, therefore, an object of the invention to provide a surface marker for use in ultrasonography which provides a distinct image on a video monitor or permanent recording media which locates the position of the transducer with respect to the position of the marker on the surface of the tissue being examined.

It is yet another object of the invention to provide a such a marker which does not obscure underlying ultrasound tissue detail.

It is still another object of the invention to provide a marker that will conform to the surface of the anatomical part to which it is applied and which will remain fixed in place during the ultrasound examination.

SUMMARY OF THE INVENTION

The present invention meets these and other objects by providing, in one aspect, a surface marker for use in ultrasound examination. The marker is placed on the surface of a tissue structure to be examined by ultrasound and comprises a material which attenuates a portion of the sonic energy applied to a field including the tissue structure and the marker. The marker thereby projects a shadow of reduced sonic energy into the tissue underlying the marker. The shadow projected by the marker is visible on a video monitor or on permanent recording media typically used in connection with ultrasound examination.

The linear nature of the shadow projected by the marker and the shadow pattern result from material from which the marker is formed and the width, thickness, overall shape and configuration (distribution of material within the overall shape) of the marker. The shadow is readily and immediately apparent on either the monitor or the recording media. Moreover, the linear or beam-like nature of the shadow and the pattern of the shadow is not representative of the images generated by any normal or abnormal tissue elements present on the surface of the tissue structure being examined. Thus, the technologist performing the examination cannot confuse the marker shadow with the image cast by surface tissue elements.

In the preferred embodiment of the invention, the marker attenuates only a limited portion of the sound energy so that diagnostic tissue detail within the shadow projected by the marker is preserved. Thus, the material from which the marker is formed and the marker's thickness, width, configuration and shape must be selected so that only a portion of the sound energy applied to the marker is attenuated. In addition to these considerations, the material comprising the marker and its thickness must be selected so that the marker is sufficiently flexible to conform to the surface of the anatomical part to which the marker is applied. The marker must also be compatible with the aqueous environment presented by the gel and durable enough to withstand repeated physical contact with the transducer head while the technologist is performing the ultrasound examination.

A broad range of materials are suitable for absorbing, scattering or otherwise attenuating the sound energy applied to the marker, including thermoplastic polymers, metals, metallic foils such as aluminized Mylar, plastic foam materials, paper and cardboard. In the preferred embodiment of the invention the material is thermoplastic ethylene vinyl acetate copolymer.

In a second aspect, the invention provides a method for ultrasound examination. The method includes the steps of placing a marker on the surface of a tissue structure to examined, and applying sonic energy to a field including the marker and the tissue structure. The marker is used to attenuate at least a portion of the sonic energy applied to the field so that the marker projects a shadow of reduced sonic energy into the underlying tissue to provide an ultrasound image of the marker along with and the underlying tissue structure. In a preferred embodiment of the invention, the shadow projected by the marker is used to locate a specified area within the tissue structure in relationship to the position of the marker on the surface.

DETAILED DESCRIPTION OF THE INVENTION

Figure 1:
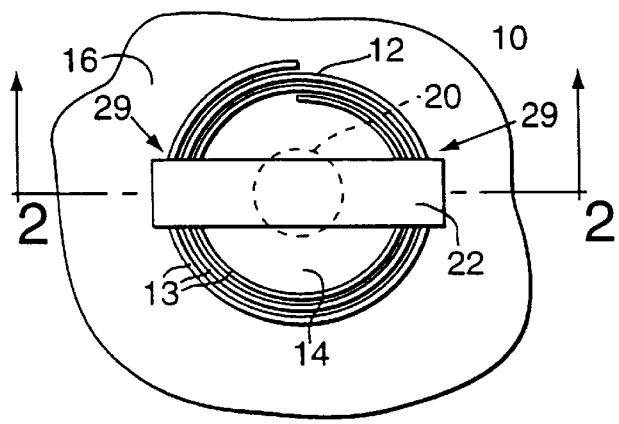
FIG. 1 is a schematic plan view of an ultrasound transducer and a surface marker embodying the invention placed on the surface of a tissue structure and vertically aligned with a clinically relevant area within the tissue structure.
Figure 2:
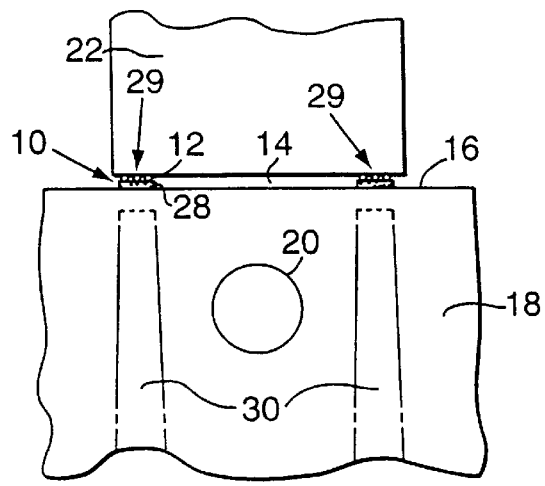
FIG. 2 is a cross-sectional view taken along the lines 2—2 of FIG. 1.
Figure 7:
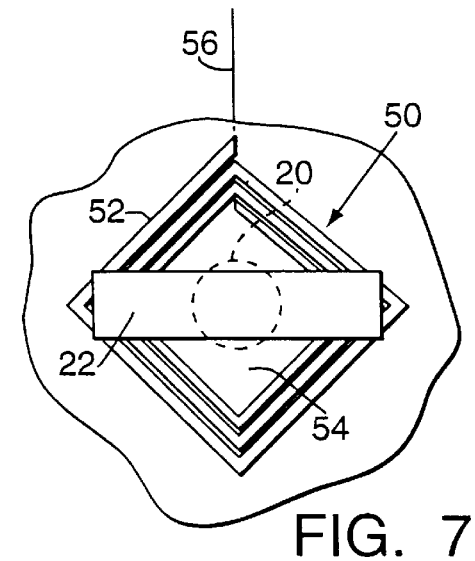
FIG. 7 is a top plan view of third embodiment of the marker taught by the invention.

A marker for use in ultrasound examination and embodying the invention is illustrated in FIGS. 1 and 2. A method of ultrasound examination using the marker will be disclosed in conjunction with the description of the marker.

As shown in FIGS. 1 and 2, the marker, generally designated 10, comprises a spiral-shaped member 12 defined by a plurality of spaced beads 13, 13.

The spiral member 12 defines a central aperture 14. The marker is shown positioned on the surface of the skin 16 lying above a tissue structure 18, which may be any anatomical part that is typically subject to ultrasound examination. In the illustrated embodiment of the invention, the tissue structure 18 includes an area of clinical interest 20, such as a tumor or cyst, the position of which has been at least approximately located by some other means, such as by palpating the tissue structure.

The marker is used in conjunction with standard ultrasound equipment to image the tissue structure and, in particular, the area 20. As described above, the equipment used in ultrasound examination typically includes a transducer, such as the illustrated transducer 22, which generates low energy sonic energy and projects the energy into the underlying tissue structure 18. As noted above, sound is echoed or reflected by the various tissue elements within the structure 18, including the area 20, depending on the acoustic impedance of each particular element. The reflected sound waves are detected by the transducer head and converted to digital images stored on a recording medium and/or displayed on a video monitor.

Figure 3:
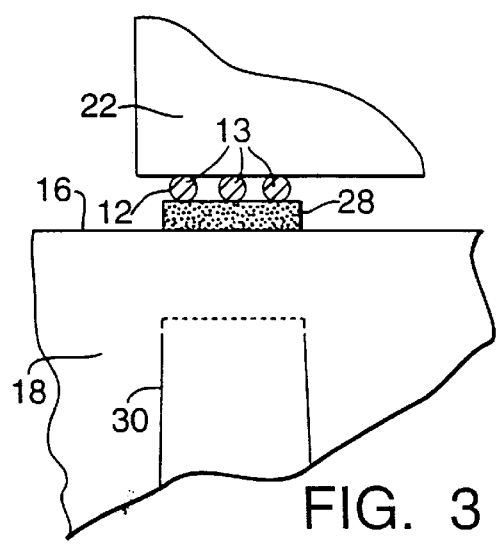
FIG. 3 is a somewhat enlarged fragmentary view of FIG. 2.

As shown in FIGS. 1–3, the marker is placed on the surface of the skin with the central aperture 14 in vertical alignment with the area 20. The marker includes a layer of adhesive 28 which fixes the marker in place on the skin. The adhesive may be any adhesive typically employed in clinical applications. However, the adhesive must be insoluble or only slightly soluble in water, since, as noted above, a layer of aqueous gel is typically applied to the surface of the skin to provide an air barrier between the skin and the transducer. In addition, the adhesive bond must have sufficient strength to withstand repeated mechanical contact between the marker and the transducer during the ultrasound examination.

Of course, the marker can be affixed to the skin by other means without departing from the scope of the invention. For example, a separate piece of water-insoluble tape dimensioned to be substantially coextensive with the marker could be used to hold the marker in place.

Once the marker is affixed in position, the transducer 22 is placed on the skin 16 and repeatedly moved back and forth in the general area of the marker. The marker 10 comprises a material having a thickness, width and configuration (i.e., distribution of material within the overall shape of the marker) which attenuates a portion of the sonic energy applied to the ultrasound field by the transducer and thereby projects a linear shadow into the underlying tissue structure. Thus, the technologist simultaneously records an image of the portion of the tissue structure 18 which is within the ultrasound field generated by the transducer 22 and the shadow projected by the marker. Such an image provides an immediate indication that a particular area of interest within the tissue structure 18, such as the area 20, is included in the field of the examination.

The spiral-shaped member 12 comprises a material and is sized, configured and shaped to project a shadow which not only meets all of the above requirements, but also a shadow which does not obscure structural detail lying within the shadow. As shown in FIG. 2, opposed portions 29, 29 of the ring-shaped member 12 disposed beneath the transducer project two linear shadows 30, 30 of reduced sonic energy into the tissue structure 18. The shadows projected by the marker are shown schematically in FIG. 2 and as an actual recorded ultrasound image in FIGS. 4 and 5.

Figure 4:
FIG. 4 is an actual ultrasound image of superficial soft tissue and including the marker illustrated in FIG. 1.
Figure 5:
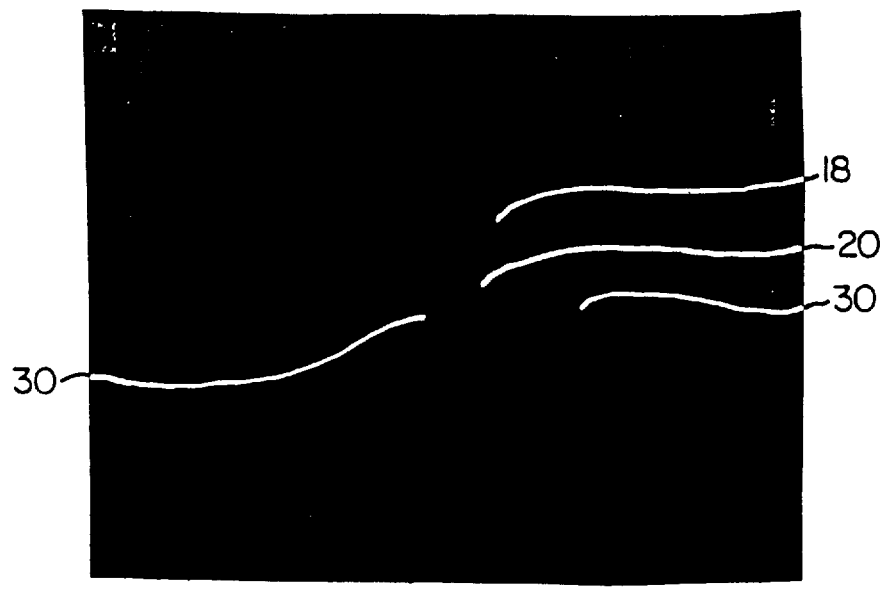
FIG. 5 is an actual ultrasound image with tissue imaging deep into the abdomen and including the marker illustrated in FIG. 1.

As illustrated on the recorded images in FIGS. 4 and 5, the linear shadows 30, 30 projected by the marker are diffuse just below the surface of the skin 16. This effect is caused by the acoustic impedance of the spaced beads 13, 13 which define the spiral member 12. Deeper into the tissue structure 18, the shadows begin to coalesce; however, the shadows never become so dark as to obscure tissue detail located within the shadows. The shadow pattern projected by the marker is not representative of ultrasound images generated by any normal or abnormal tissue elements present on the surface of the tissue structures typically subjected to ultrasound examination. Thus, the technologist performing the examination cannot confuse the marker shadow with images produced by such elements.

Since the central aperture 14 is vertically aligned with the area 20, the ultrasound image of this area is positioned between the shadows 30, 30 projected by the opposed portions 29, 29 of the spiral member. This is illustrated schematically in FIG. 2. FIGS. 4 and 5 are actual radiographic records which include an image of the area 20. As can be seen in the film, the acoustical impedance of the area 20 differs from that of the surrounding tissue 18 and may, therefore, represent a cyst. The ultrasound equipment provides a depth scale on the right hand side of the image as a standard feature. Thus, the recorded image not only indicates that the area 20 is positioned directly beneath the central aperture 14, but also indicates how deep the area 20 lies within the tissue structure 18.

Furthermore, since the area 20 is aligned with the aperture 14, the marker provides an accurate site location for entry of a needle or tracer in cases where a biopsy of the area 20 is required.

In the preferred embodiment of the invention, the spiral member 12 comprises a thermoplastic ethylene-vinyl acetate copolymer typically used as a hot melt adhesive. A particularly suitable copolymer of this kind is available from the H. B. Fuller Co. under the registered trademark RAKOLL®. The copolymer is flexible enough to conform to most anatomical parts and has sufficient mechanical integrity to withstand repeated contact with the transducer. Moreover, a marker formed from this material can be made in varying thicknesses and widths, and distributed in a variety of configurations (e.g., spiral, ring-shaped, perforated, grid-shaped, etc.). Thus, the degree of attenuation provided by the marker can be precisely controlled. Finally, the copolymer can be used to form a marker of almost any overall shape (e.g., circular, rectangular, diamond-shaped, etc.), thus providing markers useful in a wide variety of applications.

In the illustrated embodiment, the spiral member 12 has a thickness of about 1 mm to about 1.25 mm and an overall width of about 2.5 cm to about 3.0 cm.

The member defines a central opening of about 2 cm and the spacing between each coil comprising the spiral member is about 0.5 mm. A marker having these dimensions projects a distinct shadow but one which does not obscure tissue detail, as illustrated on the ultrasound records of FIGS. 4 and 5.

Limiting the thickness of the marker to about 2 mm or less avoids the possibility that the marker will be dislodge by the transducer during the examination as it is repeatedly passed over the marker. A marker of substantially greater thickness with edges well above the skin surface would catch on the edge of the transducer. Even if such a thick marker were not dislodged, it would interfere with the free movement of the transducer and, accordingly, the quality of the ultrasound examination. Further, it has been found that a marker with a thickness above about 3 to 4 mm will create artifactual changes on the ultrasound image.

The overall diameter of the marker 10 and the diameter of the central opening 14 is selected based on the width of the transducer 22. Most transducers in common use include a linear array of individual transducer elements mounted within a rectangular-shaped housing approximately 2 cm wide and about 5 cm in length. With a diameter of 2.5 to 3.0 cm, the opposed portions 29, 29 of the spiral member 12 are simultaneously contacted by the transducer, as is shown in FIG. 1. Thus, the laterally displaced shadows 30, 30 projected by the marker 10 are within the ultrasound field covered by the transducer. Further, with a marker diameter in this range, the central aperture can have a diameter of about 2 cm, which is large enough to encompass most areas of particular clinical interest located within the tissue structure being examined.

The ultrasound markers taught by the invention may be formed from a number of other suitable materials, including other thermoplastic polymers, such as polyethylene and polyethylene-ethylacrylate polymers. Other suitable materials include thin pieces of metal, particularly aluminum, metallic foils such as aluminized Mylar, polystyrene and other plastic foam materials, paper and cardboard.

Figure 6:
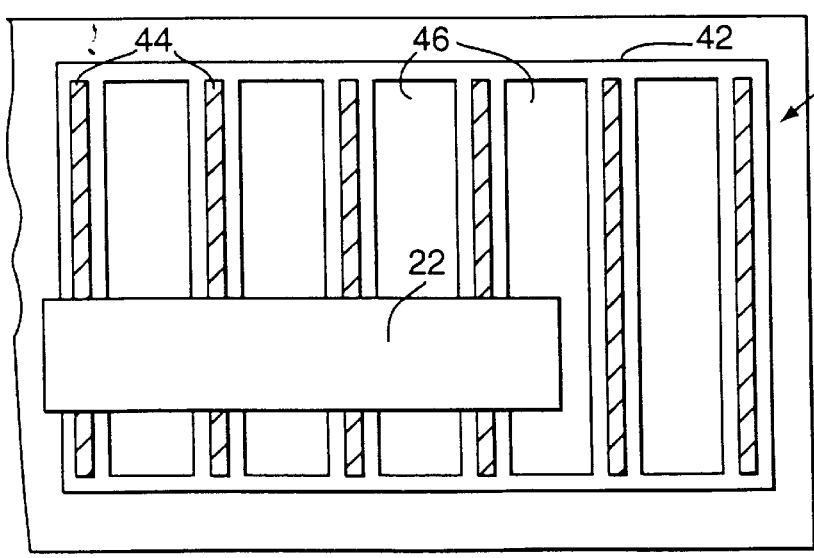
FIG. 6 is a top plan view of an alternative embodiment of a marker taught by the invention.

It should understood that the marker is not limited to the particular configuration and dimensions illustrated in FIGS. 1 and 2. The shape of the marker is dictated by the particular shadow pattern that is desired. For example, FIG. 6 illustrates a marker 40 comprising a rectangular member 42 and a series of parallel segments or strips 44, 44 transversing a central aperture 46. The strips are several centimeters long and are spaced at intervals of about 1 cm. The marker is placed on the surface of the skin with the strips aligned with the longitudinal anatomic axis of the patient. Thus, the strips 44, 44 represent a Y axis positional guide. The corresponding horizontal or X axis is determined by positioning the rectangular transducer head transversely on the patient at 90° to the Y axis. When imaged, the strips 44, 44 project a series of corresponding, equally spaced parallel shadows into the underlying tissue structure. If there is an area of particular clinical interest in the tissue structure being examined, the parallel shadows projected by the marker 40 allow the technologist to precisely determine where the area is located with respect to the central aperture 46. The strips 44, 44 may be numerically defined to assist in identifying the precise location of the area of interest within the field.

Since all of the markers taught by the invention are formed from non-toxic materials and are adhered with a water insoluble adhesive, the aqueous gel may be removed after the examination and the marker left in place on the surface of the skin for subsequent examination of the same area, if this is considered necessary.

Other shapes which have been found to be particularly useful are those that indicate the transverse or longitudinal position of the transducer head with respect to the patient. FIG. 6 illustrates a marker 50 which is particularly useful for this purpose. The marker 50 comprises a diamond-shaped member 52 which defines a correspondingly-shaped opening 54. The marker 50 is placed on the surface of the patient's skin with the longitudinal axis 56 of the diamond aligned with the longitudinal axis of the patient. The distance between the shadows projected by the member 52 provides the technologist with an indication of the position of the transducer with respect to the member and, therefore, the patient.

While preferred embodiments have been shown and described, various modifications and substitutions may be made without departing from the spirit and scope of the invention. Accordingly, it is to be understood that the present invention has been described by way of example and not by limitation.

I claim:

1. A surface marker for use in ultrasound examination, said marker comprising a material and having a thickness, width, shape and configuration such that the marker attenuates a portion of the sonic energy applied to an ultrasound field including the marker and tissue underlying the marker, wherein the marker projects at least one shadow of reduced sonic energy into tissue underlying the marker without obscuring diagnostic tissue detail within the shadow.

2. The marker of claim 1, wherein the material attenuates sufficient ultrasound energy to provide a shadow visible on a video display.

3. The marker of claim 1, wherein the material attenuates sufficient sonic energy to provide a shadow detectable on permanent recording media.

4. The marker of claim 1, wherein the thickness of the material does not produce artifactual images and/or surface irregularities.

5. The marker of claim 1, wherein the thickness of the material is in the range of from about 1 mm to about 2 mm.

6. The marker of claim 1 further comprising means for retaining the marker in a fixed position on the surface during the ultrasound examination.

7. The marker of claim 6, wherein the means for retaining comprises adhesive applied to at least on surface of the marker.

8. The marker of claim 6, wherein the material and the adhesive are waterproof.

9. The marker of claim 1, wherein the marker defines a central opening.

10. The marker of claim 1 comprising a spiral member, said spiral member defined by a plurality of spaced beads, said beads projecting two laterally spaced shadows into tissue underlying the marker when ultrasound energy is applied to a field including the marker and the underlying tissue.

11. The marker of claim 1 comprising a series of parallel strips, said strips projecting a series of corresponding, equally spaced shadows into tissue underlying the marker when ultrasound energy is applied to a field including the marker.

12. The marker of claim 1 defining differing longitudinal and transverse dimensions, said differing dimensions indicating the orientation of the marker with respect to the surface.

13. The marker of claim 1, wherein the marker comprises an ethylenevinyl acetate copolymer.

14. A method for ultrasound examination, said method comprising the steps of:

placing a marker on the surface of the tissue structure to examined;

applying sonic energy to the marker and the tissue structure;

using the marker to attenuate a portion of the sonic energy applied thereto, the marker thereby projecting a shadow of reduced sonic energy in tissue underlying the marker without obscuring diagnostic tissue detail within the shadow; and locating a specified area within the tissue structure using the shadow projected by the marker.

* * * * *